(12) United States Patent
White et al.

(10) Patent No.: US 11,578,442 B2
(45) Date of Patent: Feb. 14, 2023

(54) STENT GRAFTS, MANDRELS, AND METHODS OF USING SAME

(71) Applicant: Los Angeles Biomedical Research Institute at Harbor-UCLA Medical Center, Torrance, CA (US)

(72) Inventors: Rodney White, Torrance, CA (US); George Kopchok, Torrance, CA (US); Carlos Donayre, Torrance, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 650 days.

(21) Appl. No.: 16/606,695

(22) PCT Filed: Apr. 20, 2018

(86) PCT No.: PCT/US2018/028597
§ 371 (c)(1),
(2) Date: Oct. 18, 2019

(87) PCT Pub. No.: WO2018/195442
PCT Pub. Date: Oct. 25, 2018

(65) Prior Publication Data
US 2020/0121444 A1 Apr. 23, 2020

Related U.S. Application Data

(60) Provisional application No. 62/488,640, filed on Apr. 21, 2017.

(51) Int. Cl.
| D05B 91/06 | (2006.01) |
| A61F 2/07 | (2013.01) |
| B21F 45/00 | (2006.01) |

(52) U.S. Cl.
CPC ............... *D05B 91/06* (2013.01); *A61F 2/07* (2013.01); *B21F 45/008* (2013.01); *A61F 2240/001* (2013.01); *A61F 2240/002* (2013.01); *A61F 2250/0039* (2013.01)

(58) Field of Classification Search
CPC .......... D05B 3/20; D05B 35/10; D05B 35/12; D05B 35/02; D05B 35/06
See application file for complete search history.

(56) References Cited

U.S. PATENT DOCUMENTS

| 2,189,045 | A | * | 2/1940 | Prazak, Jr. | D05B 3/20 112/104 |
| 2,628,581 | A | * | 2/1953 | Harris | A45B 25/18 135/33.5 |
| 4,289,083 | A | * | 9/1981 | Ciucani | D05B 3/04 112/60 |
| 4,730,566 | A | * | 3/1988 | Brophy | D05B 3/20 112/113 |
| 5,458,073 | A | * | 10/1995 | Harada | D05B 55/06 112/63 |
| 8,302,548 | B2 | * | 11/2012 | Asao | D05B 3/02 112/309 |
| 2004/0073300 | A1 | * | 4/2004 | Chouinard | D04C 3/48 623/1.53 |

(Continued)

*Primary Examiner* — Danny Worrell
(74) *Attorney, Agent, or Firm* — Sheppard Mullin Richter & Hampton LLP

(57) ABSTRACT

Described are stent grafts with at least on branch and mandrels used to form the stent grafts. Methods of making and using them are also described.

6 Claims, 8 Drawing Sheets

(56) References Cited

U.S. PATENT DOCUMENTS

| | | | |
|---|---|---|---|
| 2009/0043373 A1* | 2/2009 | Arnault De La Menardiere | A61F 2/04 623/1.35 |
| 2010/0057096 A1* | 3/2010 | Wolf | A61F 2/954 604/8 |
| 2010/0249899 A1* | 9/2010 | Chuter | A61F 2/07 623/1.13 |
| 2011/0056350 A1* | 3/2011 | Gale | B23K 26/38 83/451 |
| 2012/0323303 A1* | 12/2012 | Ivancev | A61F 2/07 623/1.13 |
| 2013/0046371 A1* | 2/2013 | Greenberg | A61F 2/06 623/1.11 |
| 2014/0236280 A1* | 8/2014 | Havel | D05B 21/00 623/1.13 |
| 2015/0157444 A1* | 6/2015 | Cully | B29C 53/083 264/296 |
| 2020/0121444 A1* | 4/2020 | White | B21D 37/00 |

* cited by examiner

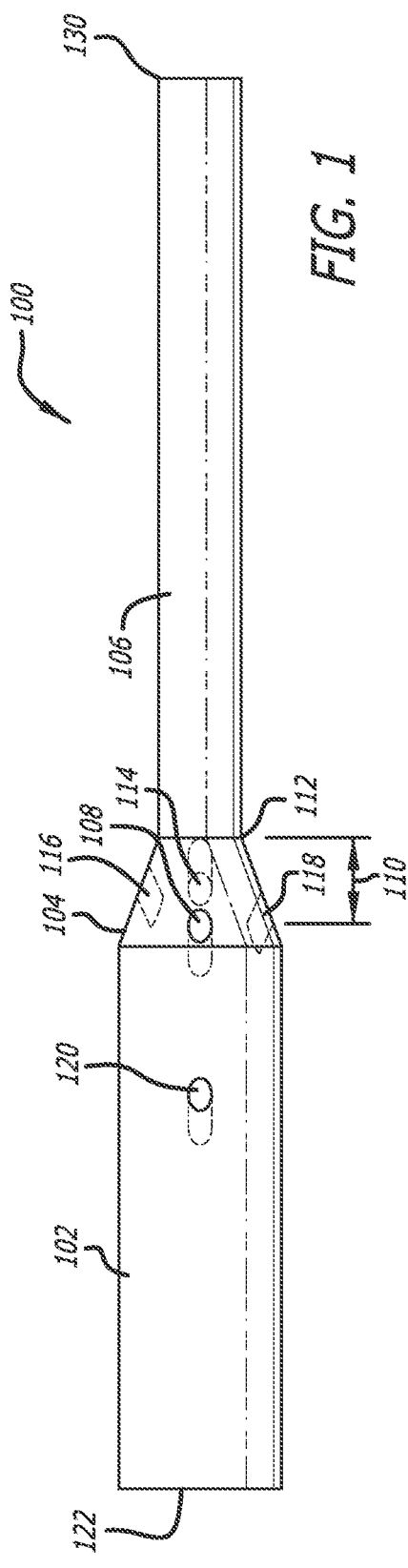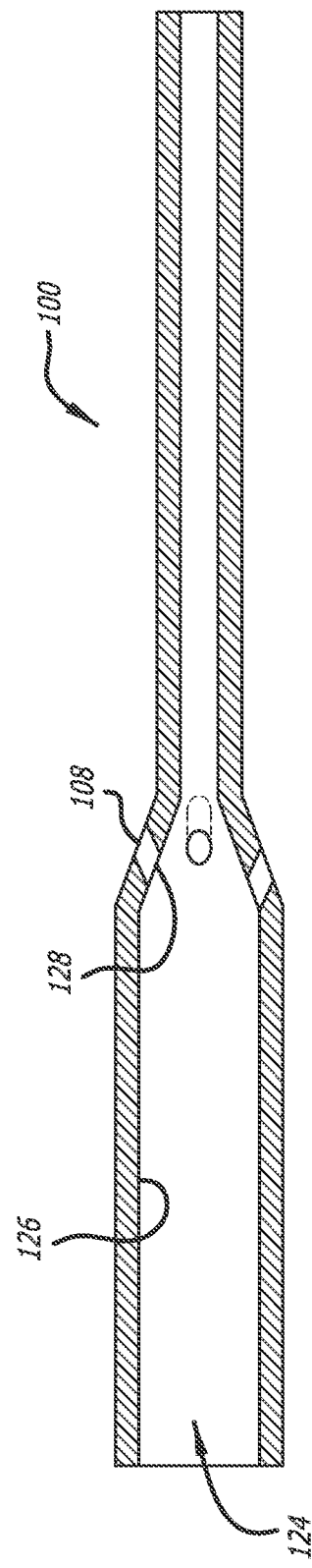

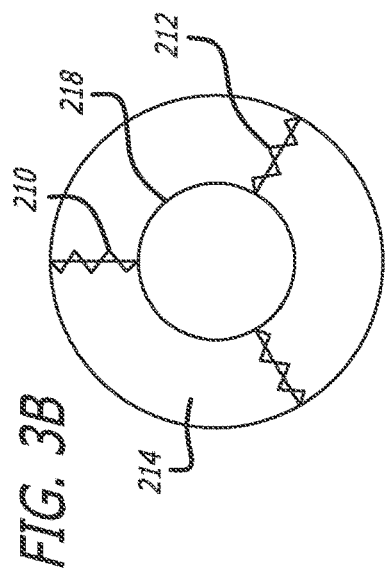
FIG. 3B
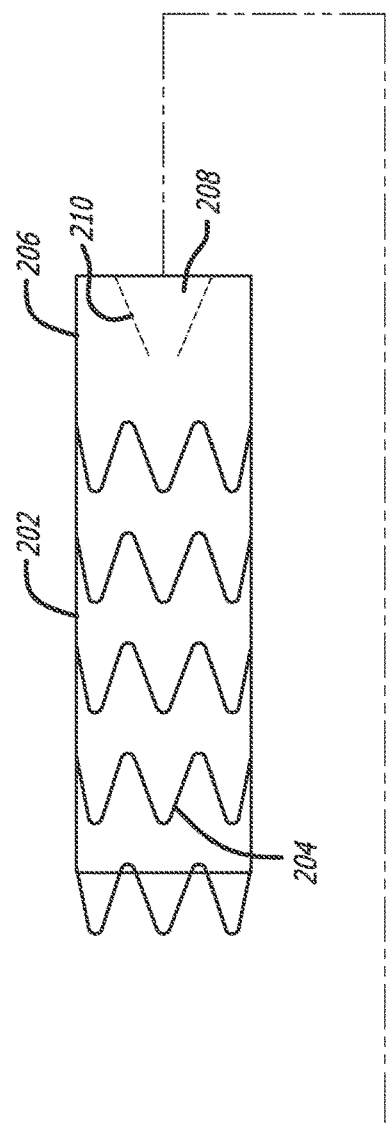
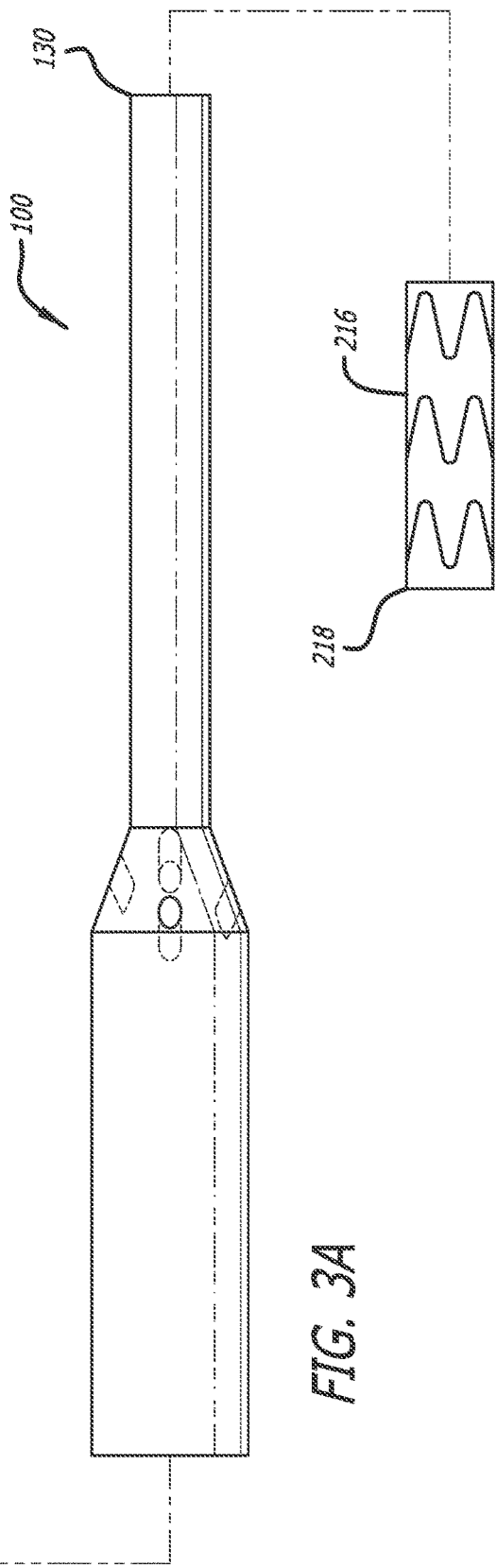
FIG. 3A

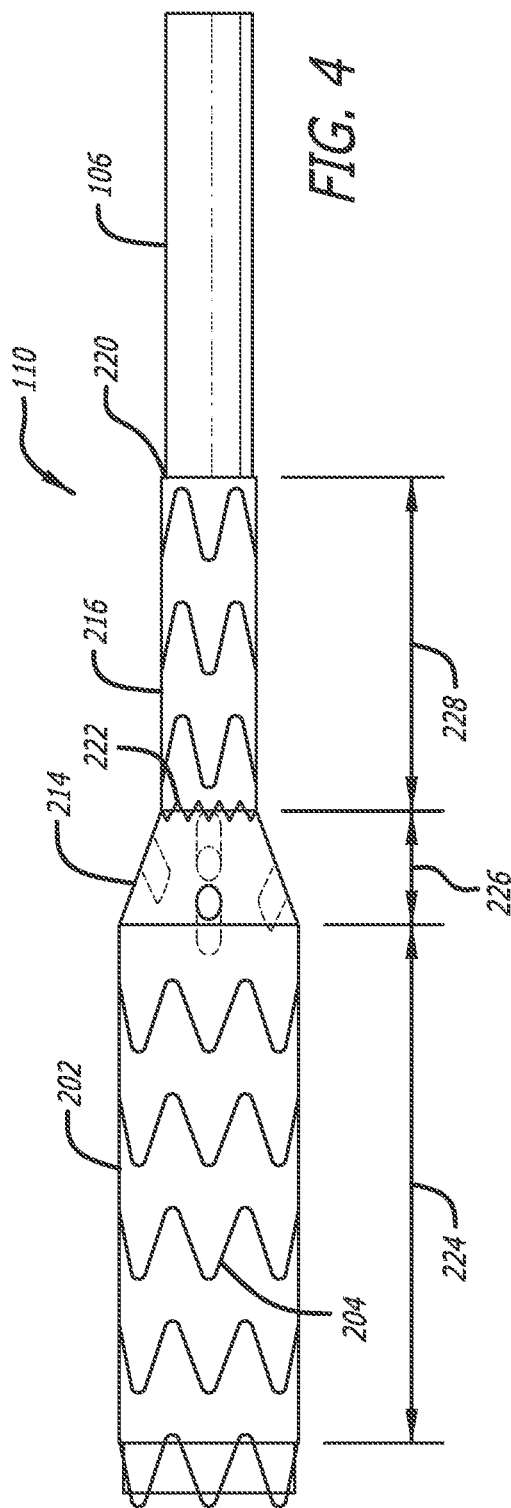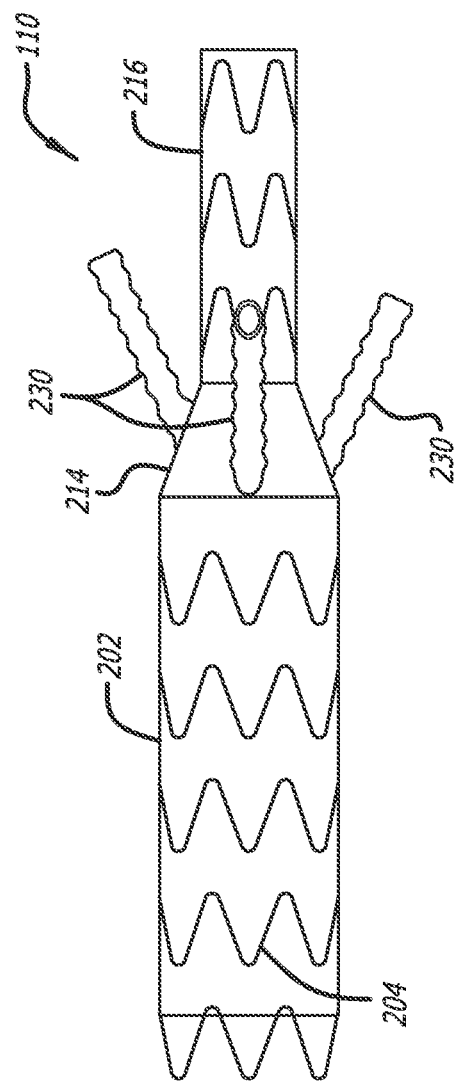

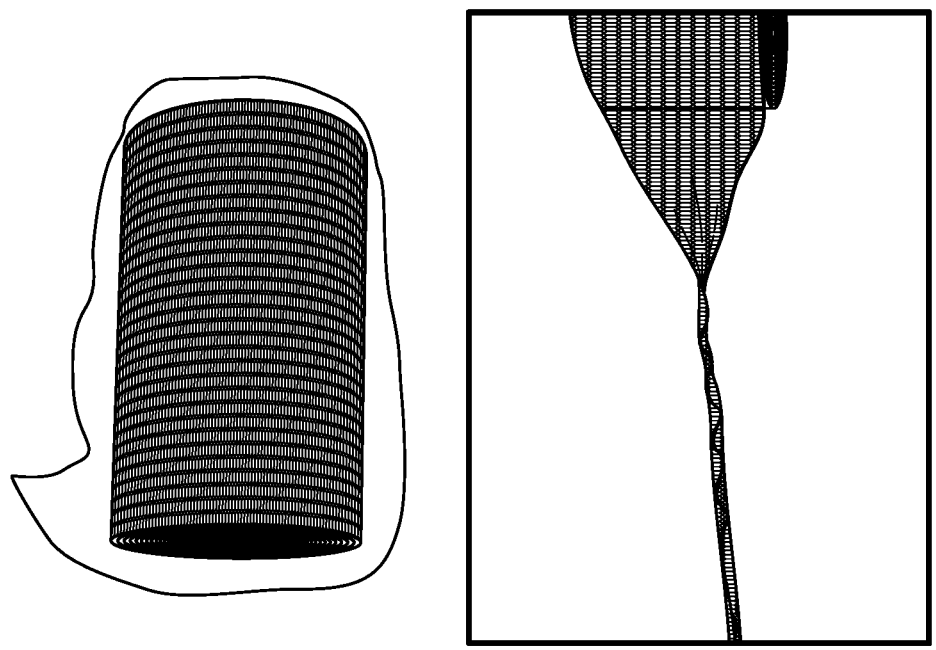
FIG. 6I
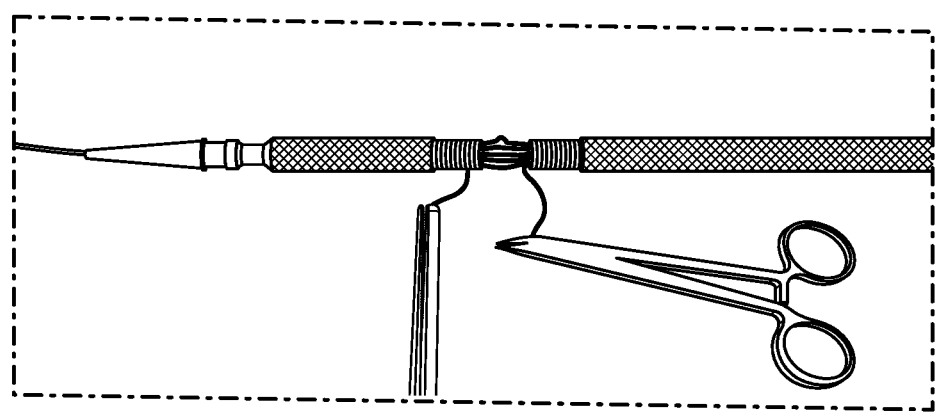
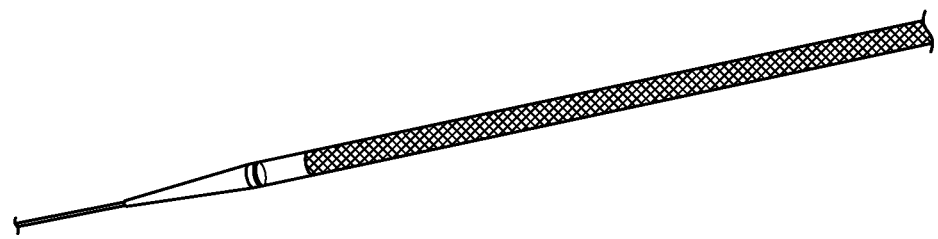
FIG. 6J

STENT GRAFTS, MANDRELS, AND METHODS OF USING SAME

CROSS REFERENCE TO RELATED APPLICATIONS

This application is the United States National Stage Application of International Application Ser. Number PCT/US2018/028597, filed Apr. 20, 2018, which claims the benefit under 35 U.S.C. § 119(e) of United States Provisional Application Ser. Number 62/488,640, filed Apr. 21,2017, the contents of each of which are incorporated by reference in their entirety into the present disclosure.

FIELD

The present application describes branched stent grafts.

SUMMARY

Described herein are branched stent grafts, or multi-branched stent grafts. These stent grafts can be custom formed or individualized using an in-line mandrel.

In some embodiments, stent graft formation mandrels are described. These mandrels can include a substantially cylindrical body including a proximal portion, a tapered portion, and a distal portion. In one embodiment, the proximal portion has a larger diameter than the distal portion. In another embodiment, the tapered portion includes a first hole at a distance from the distal end of the tapered portion and at least one additional hole at a different distance from the distal end of the tapered portion than the first hole.

In some embodiments, the stent graft formation mandrel can include four holes in the tapered portion.

In other embodiments, the mandrel's substantially cylindrical body can be formed of a polymer, a metal, or a combination thereof. The polymer, the metal or both can be formed of medical grade material.

In some embodiments, the mandrel's substantially cylindrical body can include an internal lumen in fluid communication with the first hole or the at least one additional hole. This lumen can span the entire length of the mandrel. The mandrel can further include one or more guide tubes configured to feed into the mandrel's internal lumen and out the first hole or the at least one additional hole. This guide tube can aid in supporting branch stent grafts being attached to a stent graft's main body.

In some embodiments, the mandrel's distal portion is longer than the proximal portion. Further, the mandrel can include at least one hole in the distal portion or the proximal portion.

Stent grafts are also described that can include a substantially cylindrical body including a proximal portion, a tapered portion, and a distal portion. The proximal portion in some embodiments can have a larger diameter than the distal portion. Further, the tapered portion can include at least one branch stent graft.

In some embodiments, the stent graft's tapered portion can include two, three, or more branch stent grafts.

The stent graft's tapered portion can be formed by cutting sections out of the proximal portion to form edges and sewing the edges together. In some embodiments, two, three, four or more section can be cut or otherwise removed from the stent graft. The sections can be substantially triangular in shape.

In some embodiments, branch grafts can be attached to the substantially cylindrical body at a hole formed at a predetermined location using a mandrel as herein described.

Stent grafts described can also include at least one branch graft on the proximal portion, on the distal portion, or both.

Methods of forming the stent grafts are also described. Methods can include suturing a branch graft into a hole in a tapered portion of a substantially cylindrical stent graft body. The methods can further include suturing at least one additional branch graft into at least one additional hole in the tapered portion.

The methods can include the step of forming holes in the tapered portion of the stent grafts. The holes can be formed by aligning a mandrel within the substantially cylindrical stent graft body that includes a pilot hole where the hole is to be located. At least one additional hole can be formed by aligning the mandrel within the substantially cylindrical stent graft body that includes a pilot hole where the at least one additional hole is to be located.

Holes and branch grafts described herein can be placed at predetermined locations on the stent graft, for example in the tapered portion. However, other locations may be appropriate. In some embodiments, the location of the holes can be determined using medical imagining techniques.

In some embodiments, the substantially cylindrical stent graft body can be formed by suturing a larger diameter proximal stent graft and a smaller diameter distal stent graft together.

The stent grafts described herein can be loaded into a catheter for insertion into a luminal space such as a vessel.

BRIEF DESCRIPTION OF THE DRAWINGS

FIG. 1 illustrates a mandrel used to form a branched stent graft as described herein.

FIG. 2 is a cross-sectional view of the mandrel illustrated in FIG. 1.

FIG. 3A illustrates how a proximal portion and a distal portion are inserted onto a mandrel and how tapered section is formed. FIG. 3B illustrates the distal end of the proximal section showing a non-limiting embodiment of suturing of a tapered section.

FIG. 4 illustrates joining of a distal section to a tapered section and determining of a hole location using a mandrel.

FIG. 5. illustrates an embodiment of a multi-branched stent graft as described herein.

FIG. 6A-6J illustrate the use of a fabrication mandrel to prepare a multi-branched stent graft.

DETAILED DESCRIPTION

Figure 6A:
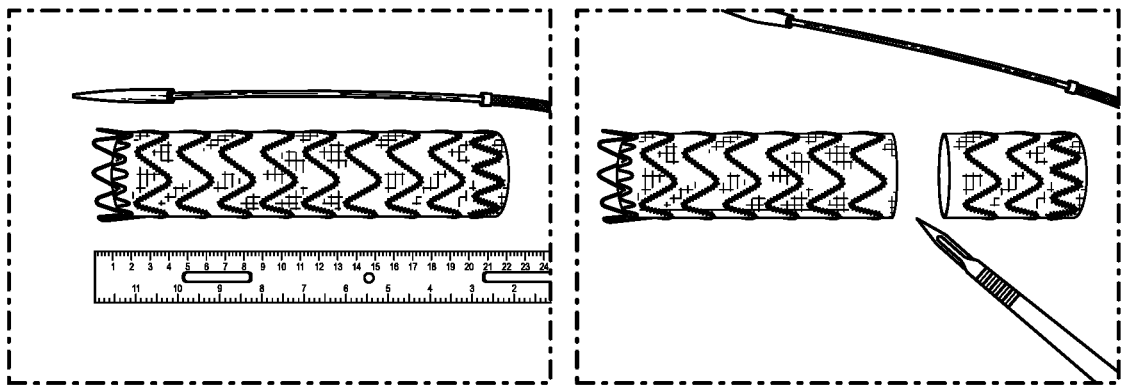

Described herein generally are stent grafts, in particular branched stent grafts. In some embodiments, the stent grafts can be multi-branched stent grafts. These stent grafts can be custom formed or individualized using the herein-described in-line mandrel.

Described herein are fabrication mandrels used to form stent grafts. These fabrication mandrels can be used to form patient-specific stent grafts. In one embodiment, the mandrels can be used to form stent grafts, for example patient-specific stent grafts, for the treatment of Type IV thoracoabdominal aortic disease.

Type IV thoracoabdominal aortic aneurysms (TAAAs) represent a proximal extension of paravisceral aortic aneurysms, starting at the diaphragmatic hiatus with involvement of the celiac axis, superior mesenteric artery and renal arteries. Thoracoabdominal aortic aneurysms involve the visceral arteries and some extent of the thoracic aorta. With this complex anatomy, any type of repair is generally more complex due to the need to incorporate these vessels into the repair, while minimizing the risk of end-organ ischemia. Commercially available devices cannot reproducibly treat Type IV thoracoabdominal aortic aneurysms.

Open repair of Types I to III thoracoabdominal aortic aneurysms has been associated with high mortality and morbidity. Endovascular aortic aneurysm repair (EVAR) has gained widespread acceptance and is currently considered the first treatment option for most patients with abdominal aortic aneurysms. Prospective randomized trials have demonstrated several short-term advantages of EVAR over open conventional repair, including less blood loss, operative time, hospital stay, mortality and morbidity.

Several anatomical constraints limit the use of endovascular stent grafts in patients with complex aortic aneurysms. The presence of short infra-renal aortic neck, severe angulation or involvement of the visceral arteries limits applications of endovascular approaches. In these patients, open conventional repair remains the standard treatment, but technical complexity increases with more extensive aneurysm or dissection, higher clamp site, prolonged visceral ischemia, and more extensive reconstruction are common.

The application of endovascular stent grafts to treat abdominal aortic aneurysms can be limited by anatomical factors in nearly 50% of patients. These anatomical constraints frequently include aneurysms with short or angulated necks or involvement of the renal, visceral and internal iliac arteries. Fenestrated stent grafts were introduced as less-invasive alternatives to treat complex aneurysms in higher risk patients using total endovascular techniques. These stent grafts contain fenestrations, which permit the incorporation of the visceral and renal arteries into the endovascular repair thereby enabling adequate proximal sealing without compromising successful aneurysm exclusion. However, fenestrated stent grafts also have disadvantages. Fenestrated stent grafts can have a disadvantage of requiring precise design, planning, and implantation, with little room for errors in any of these critical steps. Because of the narrow space between the fenestration and the target vessel, there is limited space for catheter manipulations and misalignment between the fenestration and the target vessel can result in target vessel loss. Further, when there is limited space in the aorta, the use of directional branches may be compromised by the lack of space to accommodate the aortic stent graft and the pre-sewn cuffs.

In contrast, a multi-branch stent graft as described herein can catheterize and stent graft vessels using branches that are typically longitudinally oriented to the main body of the graft. This is done with down-going branches cannulated from the brachial approach, or, less frequently, up-going branches that can be catheterized via the femoral approach. The presence of a large aortic luminal space is ideal to facilitate navigation of catheters from the side branch or cuff to the target visceral artery, eliminating the issue of misalignment that occurs with fenestrations while providing longer attachment sites for the mating stent graft.

Although the infra-renal aorta is generally the most common site for aneurysmal disease to develop, it can involve any region of the aorta and its major branches. Thus, the presently described stent grafts can be configured to be deployed and treat aneurysms in any region of the aorta and its major branches. Further, the herein described grafts can provide an endovascular alternative to open surgical repair and may also provide treatment to patients who are not candidates for open repair.

In some embodiments, the grafts can be configured for use in the thoracoabdominal aorta. In other embodiments, the grafts can be configured for use in treating ascending aortic disease with branches extending to the aortic arch vessels and continuation into the descending thoracic aorta.

The herein described stent grafts can be a wedding of two thoracic stent grafts. These wedded stent grafts can then be deployed at locations consistent with a particular patient's needs.

For endovascular delivery, the branched stent graft can then be packed into a delivery system such as a catheter. The stent grafts as described herein can be packaged into delivery systems having a size of less than about 50 Fr, less than about 40 Fr, less than about 30 Fr, less than about 25 Fr, less than about 20 Fr, less than about 15 Fr, less than about 10 Fr, between about 50 Fr and about 10 Fr, between about 30 Fr and about 20 Fr, or between about 40 Fr and about 10 Fr. In some embodiment, the stent grafts can be packed into a 25 Fr delivery system.

The herein described stent grafts can be formed using an in-line fabrication mandrel. Such a mandrel, mandrel 100, is illustrated in FIGS. 1 and 2. Mandrel 100 can be used to aid in stent graft modification, sizing, and support throughout the modifications.

Mandrel 100 can include a larger diameter, proximal portion 102, a tapered portion 104, and a smaller diameter, distal portion 106. Tapered portion 104 can include one or more holes 108. In some embodiments, tapered portion 104 can include two, three, four, five, six, seven, eight, nine, ten, eleven, twelve or more holes. In one embodiment, tapered portion 104 includes four holes. These four holes can be equally spaced around the circumference of tapered portion 104, or located in anatomical locations based on prior patient imaging.

Each hole located on tapered portion can be spaced at a different distance 110 from proximal end 112 of distal portion 106. In an embodiment with four holes in tapered section 104, each hole can be progressively farther from proximal end 112 of distal portion 106. For example, in one embodiment, first hole 114 is closest to proximal end 112 of distal portion 106, second hole 116 is next farthest from proximal end 112 of distal portion 106, third hole 118 is next farthest from proximal end 112 of distal portion 106, and hole 108 is farthest from proximal end 112 of distal portion 106. Spacing holes at different distances 110 from proximal end 112 of distal portion 106 allows for movement of a hole along tapered portion 104 by spinning mandrel 100. This movement of a hole location can assist in forming holes in a stent graft as will be described herein. In some embodiments, each hole has a different distance from the distal end of the tapered portion. In some embodiments, the stent graft formation mandrel has no holes in either the proximal portion or the distal portion.

In another embodiment, holes 112 can be formed in a spiral pattern around tapered portion 104 at slightly reduced distances from proximal end 112 of distal portion 106. In other embodiments, holes 112 can be formed in a spiral pattern around tapered portion 104 at slightly increased distances from proximal end 112 of distal portion 106. The more holes located in tapered portion 104, the more flexibility of hole position can be achieved by spinning mandrel 100.

Mandrel 100 can also include one or more additional holes 120 in proximal portion 102, distal portion 106, or both. In some embodiments, proximal portion 102 and/or distal portion 106 can include two, three, four, five, six, seven, eight, nine, ten, eleven, twelve or more holes.

In some embodiments, additional holes 120 can be formed in a spiral pattern around proximal portion 102, distal portion 106, or both at slightly reduced distances from proximal end 122 of proximal portion 102, proximal end 112 of proximal portion 102, or both.

In other embodiments, additional holes 120 can be formed in a spiral pattern around proximal portion 102, distal portion 106, or both at slightly increased distances from proximal end 122 of proximal portion 102, proximal end 112 of proximal portion 102, or both. The more holes located in proximal portion 102, distal portion 106, or both the more flexibility of hole position can be achieved by spinning mandrel 100.

Mandrel 100 can be formed with an internal lumen 124. Inner lumen 124 can be defined by inner wall 126 and can be configured to allow access to inner portion 128 of holes 108.

Mandrels can be formed of any appropriate material or combination of materials. In some embodiments, that material can be a medical grade material. Materials can include metals and polymers. Metals can include, but are not limited to, brass, steel, iron, aluminum, copper, zinc, alloys thereof, or combinations thereof. Polymers can include, but are not limited to polyurethanes, silicones, polyesters such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; carboxymethyl cellulose; synthetic and natural rubbers such as polysiloxanes, latex, polymerized isoprene, bromo isobutylene isoprene, chloro isobutylene isoprene, polychloroprene, chlorosulphonated polyethylene, ethylene propylene, ethylene propylene diene monomer, fluoro silicone, hydrogenated nitrile butadiene, polyisoprene, isobutylene isoprene butyl, methyl vinyl silicone, acrylonitrile butadiene, acrylonitrile butadiene carboxy monomer, styrene butadiene, epichlorodydrin; and combinations thereof.

Mandrels described herein can be formed using a three-dimensional printer, injection molding techniques, extrusion, casting techniques, blow molding techniques, thermoforming techniques, and the like.

Mandrels described herein can have different sizes depending on the desired size of a resulting stent graft product. In one embodiment, a mandrel can have a total length from the proximal end to the distal end can be about 250 mm, about 275 mm, about 300 mm, about 325 mm, about 350 mm, about 375 mm, about 400 mm, at least about 250 mm, at least about 300 mm, or between about 250 mm and about 400 mm.

In one embodiment, the length of a proximal portion 102 can be about 100 mm, about 110 mm, about 115 mm, about 120 mm, about 125 mm, about 130 mm, about 135 mm, about 140 mm, about 150, at least about 100 mm, at least about 120 mm, between about 100 mm and about 150 mm, or between about 120 mm and about 130 mm.

In one embodiment, the length of a distal portion 106 can be about 120 mm, about 130 mm, about 140 mm, about 150 mm, about 160 mm, about 170 mm, about 175 mm, about 180 mm, about 190 mm, about 200 mm, at least about 120 mm, at least about 150 mm, between about 120 mm and about 200 mm, or between about 170 mm and about 180 mm.

Other lengths may also be desirable if a longer or shorter stent graft is desired.

In one embodiment, the outer diameter of a proximal portion 102 can be about 35 mm, about 36 mm, about 36.5 mm, about 37 mm, about 37.5 mm, about 38 mm, about 38.5 mm, about 39 mm, about 40 mm, at least about 35 mm, at least about 37 mm, between about 35 mm and about 40 mm, or between about 36 mm and about 37 mm.

In one embodiment, the outer diameter of a distal portion 106 can be about 17 mm, about 18 mm, about 18.5 mm, about 19 mm, about 19.5 mm, about 20 mm, about 20.5 mm, about 21 mm, about 21.5 mm, at least about 22 mm, at least about 19 mm, between about 15 mm and about 20 mm, or between about 19 mm and about 20 mm.

Other outer diameters may also be desirable if a larger or smaller diameter stent graft is desired.

Mandrel 100 can assist in modifying the endoluminal graft by providing a template for the device taper to the correct diameter, aligning sequential devices that are being sutured to the main body, and providing a guide for the location and placement of side branches. In some embodiments, mandrel 100 can align the grafts and branches to aid in the suturing in a reproducible fashion.

In some embodiments as illustrated in FIGS. 3-5, a first, proximal stent graft 202 is placed over mandrel 100 at proximal portion 102. Proximal stent graft 202 can be supported along its entire length by stent struts 204 to ensure kink resistance. In other embodiments, stent grafts described herein may not have any struts at all or may have struts only on various portions of the stent graft.

In some embodiments, one stent strut is removed from the distal portion 206 of proximal stent graft 202. Then, a segment 208 is cut from distal portion 206. Segment 208 can be about 1-1.5 cm wide and about 2 cm long.

The edges 210 of segment 208 can then be sewn 212 together. In some embodiments, the edges can be sutured using a running locking 4-0 polyester braided suture in end to end fashion. Segment cutting and suturing can be repeated at least two additional times at about 120 degrees and about 240 degrees from the first cut segment in order to taper the device diameter to an appropriate size and form tapered stent graft portion 214.

Then, a smaller diameter, distal stent graft 216 can be placed over mandrel 100 from distal end 130. Proximal stent graft 202 and stent graft 216 can then be placed in juxtaposition over mandrel 100 and aligned such that distal end 218 of tapered stent graft portion 214 can be adjacent to proximal end of stent graft 216. This placement of stent graft 216 allows distal portion 106 to at least partially emanate from distal end 220 of stent graft 216.

Stay sutures 222 can be placed at the quadrants and the edges sutured. In some embodiments, the edges can be sutured using a running locking 4-0 polyester braided suture in end to end fashion.

An assembled stent graft body or sutured stent graft can include a larger diameter, proximal portion 224, a tapered portion 226, and a smaller diameter, distal portion 228.

In some embodiments, a stent can be fabricated to fit onto mandrel 100 without the formation steps described herein.

The assembled stent graft body can then be fitted with at least one branch stent graft 230 on tapered portion 226. In other embodiments, the assembled stent graft body can be fitted with two or more branch stent grafts on tapered section 226. The assembled stent graft body can in some embodiments be fitted with two, three, four, five, six, seven, eight, nine, ten, eleven, twelve or more branch stent grafts on tapered section 226.

In some embodiments, in addition to the branch stent grafts added to the tapered section, the assembled stent graft body can be configured to include two, three, four, five, six, seven, eight, nine, ten, eleven, twelve or more branch stent grafts on proximal portion 224, distal portion 228, or both.

Locations of any branch vessels that may require branch stent grafts can be predetermined from a patient's CT scan or other medical imaging technique. At least one location can be simulated on tapered portion 226. In other embodiments, two or more locations can be simulated on tapered portion 226. Other locations can be simulated using the patient specific imaging data.

Branch stent graft 230 can have a diameter of between about 4 mm and about 10 mm, about 6 mm and about 8 mm, about 4 mm, about 5 mm, about 6 mm, about 7 mm, about 8 mm, about 9 mm, about 10 mm, at least about 4 mm, or at least about 6 mm. Branch stent graft 230 can have lengths sufficient to originate at proximal portion 224, a tapered portion 226, or distal portion 228 and be located and/or secured within a desired branch vessel. In some embodiments, imaging data can be used to determine the length(s) of any branch grafts and those branch grafts can be cut to a desired length.

In some embodiments, simulating these locations can require that a hole be created or otherwise cut in the assembled stent graft body at a desired location, e.g., in tapered portion 226 and then a branch stent graft be sewn to the assembled stent graft body.

Holes can be created or otherwise cut in the assembled stent graft body, such as in tapered portion 226 using a cautery device. In one embodiment, the cautery device is one included with a stent graft. In other embodiments, the cautery device can be an Accu-Temp High Temperature Cautery device.

Holes can be created or otherwise cut at different locations by arranging the mandrel's holes at appropriate locations based on the medical image. As described above, hole 108 can be relocated by spinning mandrel 100 within the assembled stent graft body. Once a hole is located in a desired location relative to the assembled stent graft body, a hole can be cut in the assembled stent graft body using the mandrel hole as a guide.

In some embodiments, branch stent grafts 230 can be placed on tapered portion 226 for easier branch cannulation and/or to maximize radiographic imaging. In vitro device deployment in an acrylic vascular model has demonstrated that branches were more easily identified if placed in the tapered portions of the stent graft.

Visceral branches can be constructed by suturing branch grafts into the holes formed in tapered portion 226. In some embodiments, once a hole is cut in the stent graft, a guide wire or tube can be fed through the mandrel hole and the stent graft hole. A branch stent can then be fed to the hole location over the guide wire or tube. The guide wire or tube can assist in supporting the branch stent graft during attachment.

Once in place, branch graft 230 can be sutured to the assembled stent graft body at a desired hole location. In some embodiments, the branch grafts can be sutured to the assembled stent graft body using a running locking 4-0 polyester braided suture in, for example, an end to end fashion.

In one embodiment, branch grafts be have diameters from about 6 mm to about 8 mm. However, other diameters can be used depending on a particular patient's branch vessel size.

Once all the desired branch grafts have been added to the assembled stent graft body, the assembled stent graft can be slid off the distal end 130 of mandrel 100.

An assembled stent graft is illustrated in FIG. 5 including three branch grafts.

The multi-branch stent grafts, once formed, can be loaded into a catheter for implantation into a subject, such as a human.

In some embodiments, the assembly and packaging of the herein described branched stent grafts can be performed within the sterile field prior to a particular patient's surgery. In other embodiments, imaging data can be used to assemble, package and sterilize the herein described branched stent grafts remotely and the packaged and sterilized device can be delivered for surgery. In still other embodiments, the grafts can be built remotely and then sterilized prior to implantation.

In some embodiments, the branched stent grafts can be assembled by humans. In other embodiments, robotics can be used to assemble the grafts.

The present multi-branch stent grafts can have the branch grafts sewn on prior to implantation. In some embodiments, at least one of a plurality of branch stent grafts is attached to the main body of the stent graft prior to implantation. In other words, at least one branch stent graft is not simply fenestrated (holes in the graft to be cannulated after deployment). In some embodiments, one or more branch graft may be fenestrated as long as at least one branch graft is attached to the main body prior to implantation. In some embodiments, all branch grafts are attached prior to implantation. In other words, in some embodiments, the graft is completely assembled prior to implantation.

The presently described multi-branch stent grafts may exceed the durability and applicability of traditional fenestrated devices in large aneurysms as the side branches can be customized and extended into selected visceral arteries.

The presently described multi-branch stent grafts described herein may be provided in a kit. A kit can include a multi-branch stent graft as described herein and instructions for use.

In other embodiments, kits can be provided with parts in order to assemble the herein described multi-branch stent grafts and instructions for assembly and use. For example, in some embodiments, a kit can include a main body stent graft, a smaller main body stent graft, one or more branch stent grafts, suturing supplies, a mandrel as described herein, and instructions for use.

In still other embodiments, a kit can include a mandrel as described herein and instructions for use. Such a kit may require that a skilled artisan use available stent grafts to make a multi-branch stent graft as described herein. Other embodiments include a kit comprising a mandrel as described herein, suturing materials, and instructions for use.

In some embodiments, any kit described herein can include a cautery device to form holes using a mandrel.

Another kit can include different sized mandrels. A mandrel can then be selected based on the needed size of branched stent graft.

In some embodiments, mandrels described herein can be used to assemble multiple branched stent grafts. The mandrels can be cleaned and sterilized between use without substantial degradation to the mandrel. Substantial degradation is any degradation that prevents proper sewing, cutting, spinning, or the like.

The multi-branch stent grafts, mandrels, suturing materials, and kits described herein can be sterilized without substantial degradation of the implantable product. The multi-branch stent grafts, mandrels, suturing materials, and kits can be safe to at least one sterilization technique including, but not limited to gamma irradiation, pressure sterilization and/or steam sterilization.

The presently described multi-branch stent grafts and mandrels can allow a fully customizable process. Both the main body and each branch graft can be custom sized and each branch graft can be appropriately located for a particular patient's anatomy.

Further, the presently described multi-branch stent grafts and mandrels can be used to create grafts with branch grafts located on a tapered portion of the graft. This location of branch grafts makes insertion into target anatomy easier than conventional solutions.

Methods of deploying the herein described branched stent grafts can include inserting into a main vessel of interest a catheter or other delivery device that includes a branched stent graft. An appropriate imaging technique can be used to locate the end of the catheter at an appropriate location in the main vessel. Once located appropriately, the catheter sheath can be pulled off thereby revealing the branched stent graft. The stent graft then expands to the diameter prior to packing within the catheter sheath.

The proximal portion of the stent graft expands to a larger diameter than the distal portion and secures against the walls of the vessel by the radial force exerted. The smaller distal portion allows one or more branch stent grafts to deploy axially to it. A catheter used to deploy the branch vessels can be deployed into each branch stent graft through its hole in the tapered section of the main body. By navigating through the tapered section, more space is available to assist the surgeon in deploying the branch stent grafts.

Branch stent grafts not located on the tapered section are then deployed into branch vessels. This procedure may be more challenging that deploying branch stent grafts located in the tapered section.

Once all the branch stent grafts have been deployed, the insertion catheter is removed and the patient is transitioned to post-op.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1. Fabrication of Stent Graft with a Fabrication Mandrel

This example illustrates a method of fabrication using a fabrication mandrel.

The following steps were carried out to illustrate the use of a fabrication mandrel to prepare a multi-branched stent graft:

1. Deploy a larger (proximal Captiva Bare Spring) Valiant device. Cut the distal end of device to the desired length, as measured from the proximal end using a scalpel (FIG. 6A).

Figure 6B:
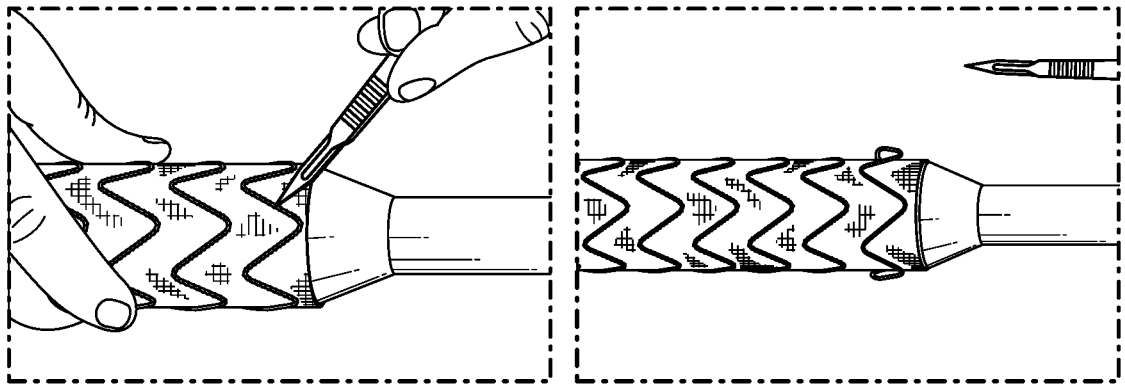

2. Place the larger proximal graft over the support mandrel and using a scalpel, remove the last, most distal, stent from the graft, leaving approximately 2.5 cm of unsupported graft material. At completion, remove any remaining suture material from graft and inspect for any damage to graft material. If any holes or damaged areas are found, repair with appropriate suture(s) (FIG. 6B).

Figure 6C:
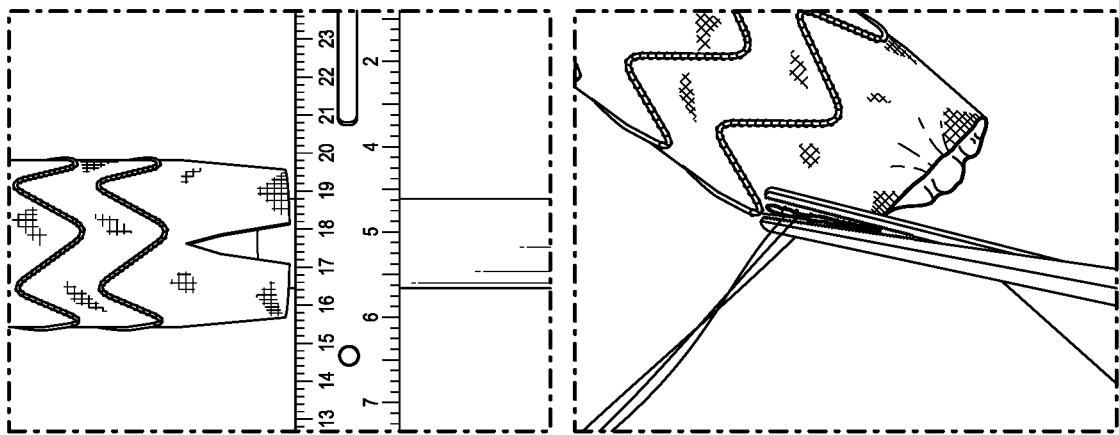

3. Cut three longitudinal wedges at approximately 0, 120 and 240 degrees that will be used to taper the graft to the desired distal diameter. The triangular wedge will be 1-1.5 cm wide and 2 cm along the length. An approximate width can be calculated using $((\pi D_1 - \pi D_2)/3 + 4$ mm$)$. The extra 4 mm is for suturing the edges. A small hemostat or vascular clamp can be used to align the edges. Use a continuous running locking suture (Braided Polyester (4-0)) along the length of the graft edges to re-oppose the wedge edges. Repeat this step two additional times to reduce the diameter leaving the reduced lumen (FIG. 6C).

4. Deploy a smaller (22-28 mm) Valiant graft and carefully remove the bare metal stent with a scalpel or shorten the device as needed to achieve appropriate distal component length using a scalpel.

Figure 6D:
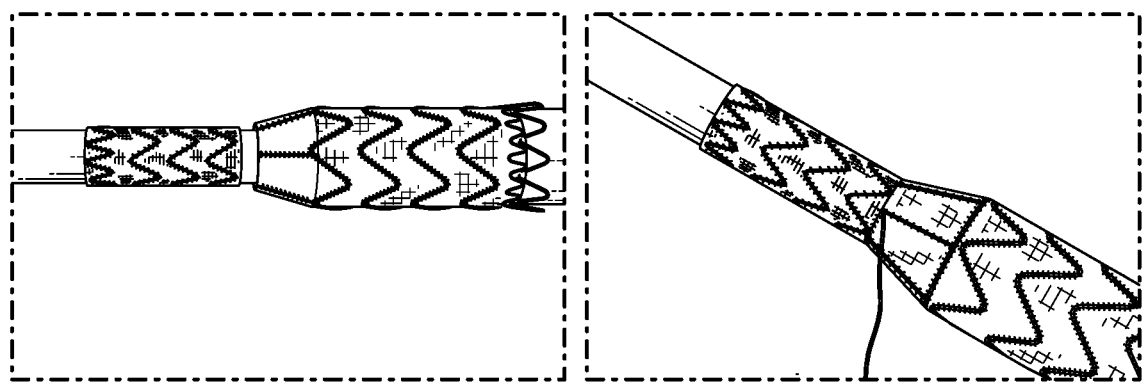

5. Align the two devices over the mandrel so the support struts and suture lines are on the same axis. Use a continuous running locking suture (Braided Polyester (4-0)) along the length graft edges in an end to end fashion to connect the two devices. Secure the suture at each quadrant. Stay sutures can be placed at each quadrant to help align the grafts. Additional U-stitching can be placed at the graft suture line. The grafts are sewn in four separate quadrants to prevent catastrophic component separation (FIG. 6D).

6. Align the proximal Valiant FIG. 8 markers and stent weld/support strut with the anterior position of the fenestrated graft to aid in the correct deployment location. This may be referred to as the 0 degree position.

Figure 6E:
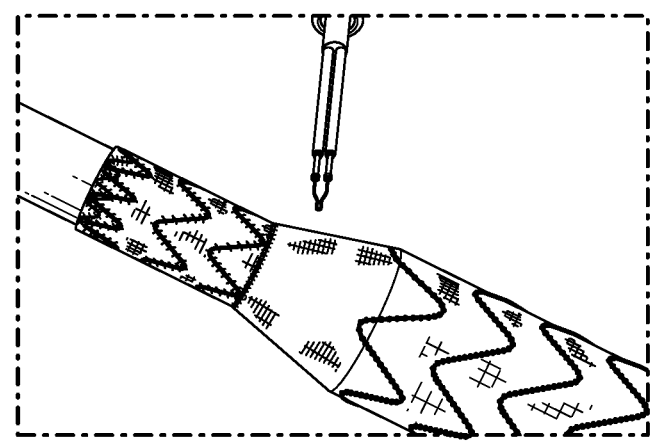

7. Use angular measurements from the CT scan to place holes at appropriate angles along the graft. To make the holes, use an Accu-Temp High Temperature Cautery (Fine Tip #844220) to cut a small hole in the tapered section of the graft. A guide may be helpful in gauging the hole diameter. See FIG. 6E.

Figure 6F:
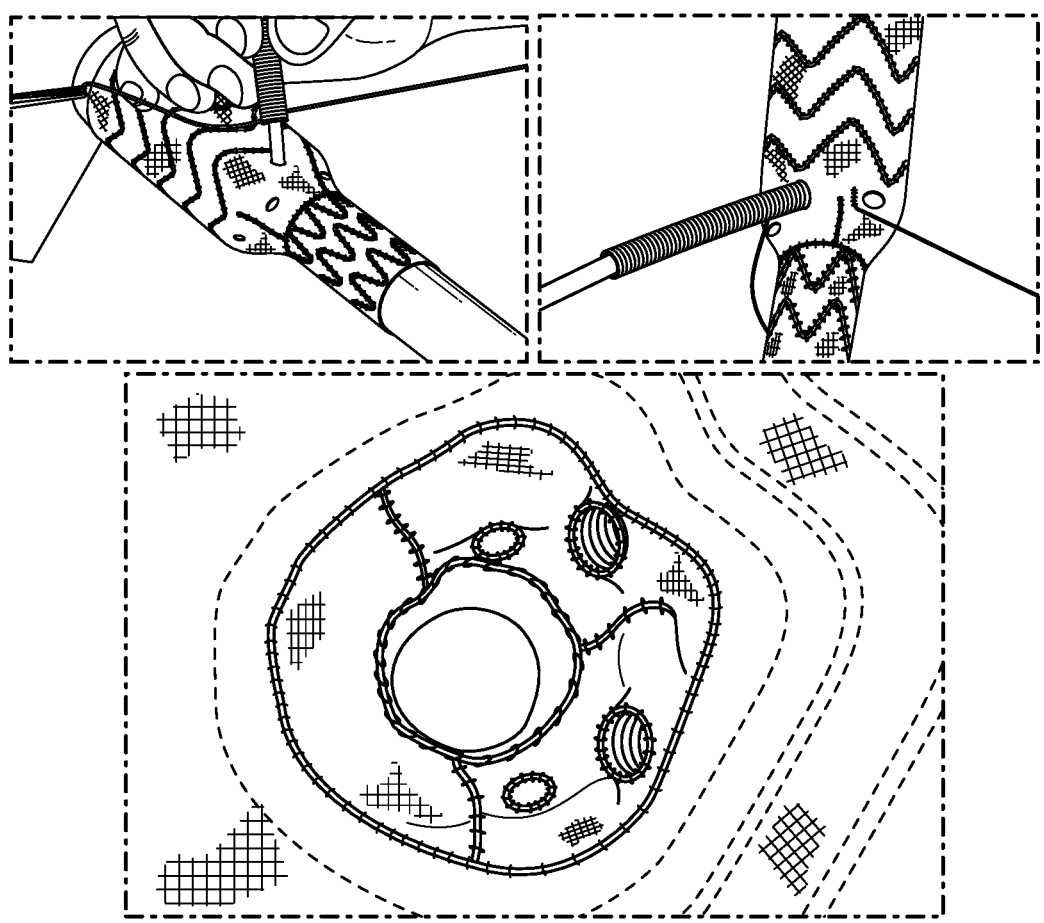

8. After the holes are completed, place a small rod or support strut through the hole and support mandrel. Place the Viabahn device over the strut to align with appropriate hole. Use a continuous running locking suture (Braided Polyester (4-0)) to attach the Viabahn device. Repeat this procedure to attach the additional branches in an anatomically appropriate location. Branches as seen from inside the device lumen are marked by arrows in FIG. 6F.

Figure 6G:
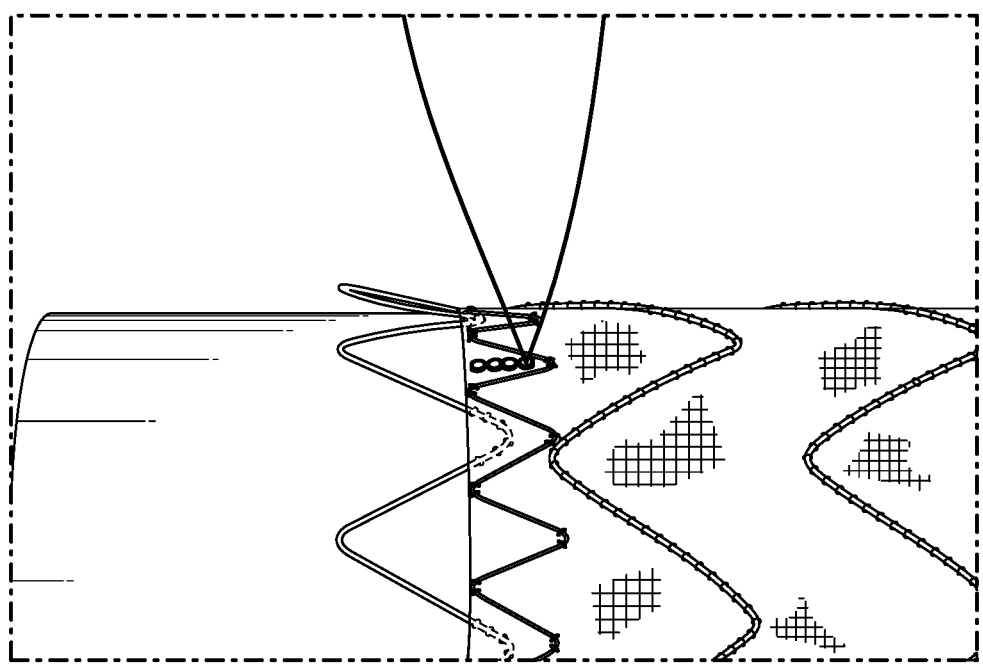

9. Remove the FIG. 8 marker from the proximal right anatomical location and attach it distal to the left marker to aid in device orientation (FIG. 6G).

10. Finished device is then repacked in a 25 Fr, 200 cm long Valiant Graft Delivery System. A 0.035 superstiff guidewire is passed through the device guidewire lumen to aid reloading process.

Figure 6H:
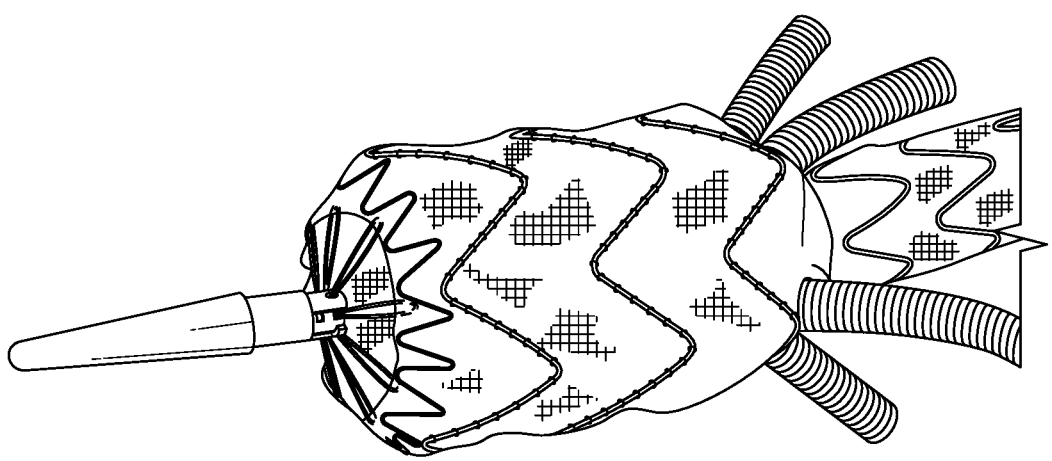

11. Recapture the struts by advancing the release hub on the delivery handle to advance and capture the struts. After all of the struts have been captured, turn the release hub clockwise to lock the system. The anterior position should correspond with the single FIG. 8 marker and stent weld/support strut. The double figure eight markers should be on the patient's left anatomical position (FIG. 6H).

12. Use Co-Flex® flexible to wrap the device along the shaft, starting at the end of the catheter tip. A cylinder or modified 3 mm syringe can be used to partially constrain the device diameter as the Co-Flex is wrapped. Wrap the loops tightly and in close proximity to protect the device while being introduced into the sheath and minimize outer diameter (FIG. 6I).

13. When near the end of the graft, verify length and cut the Viabahn if needed to fit within the delivery sheath. Continue the wrap to fully incorporate the graft.

14. Advance the delivery sheath over the device by turning the release handle clockwise. Slowly un-wrap the Co-Flex as the device enters the delivery sheath. Continue to unwrap the Co-Flex while advancing the outer delivery sheath towards the tip. Continue until the sheath mates with tip hub and the reloading step is completed (FIG. 6J).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A stent graft formation mandrel comprising:
   a substantially cylindrical body including a proximal portion, a tapered portion, and a distal portion;
   wherein the proximal portion has a larger diameter than the distal portion
   wherein the tapered portion includes a first hole at a distance from the distal end of the tapered portion and at least one additional hole at a different distance from the distal end of the tapered portion than the first hole; and
   wherein the substantially cylindrical body includes an internal lumen in fluid communication with the first hole or the at least one additional hole.

2. The stent graft formation mandrel of claim 1, including four holes in the tapered portion.

3. The stent graft formation mandrel of claim 1, wherein the substantially cylindrical body is formed of a polymer.

4. The stent graft formation mandrel of claim 1, further comprising a guide tube configured to feed into the internal lumen and out the first hole or the at least one additional hole.

5. The stent graft formation mandrel of claim 1, wherein the distal portion is longer than the proximal portion.

6. The stent graft formation mandrel of claim 1, further including at least one hole in the distal portion or the proximal portion.

* * * * *